(12) United States Patent
Hofmann

(10) Patent No.: US 6,884,797 B2
(45) Date of Patent: Apr. 26, 2005

(54) TARGETED OXIDATIVE THERAPEUTIC FORMULATION

(76) Inventor: Robert F. Hofmann, 3105 Toro Ring, Austin, TX (US) 78746

( * ) Notice: Subject to any disclaimer, the term of this patent is extended or adjusted under 35 U.S.C. 154(b) by 335 days.

(21) Appl. No.: 09/823,252

(22) Filed: Mar. 30, 2001

(65) Prior Publication Data

US 2003/0032677 A1 Feb. 13, 2003

(51) Int. Cl.$^7$ .................... A61K 31/555; A61K 31/535; A61K 31/405; A61K 31/135; A61K 31/12

(52) U.S. Cl. .................... 514/185; 514/236.2; 514/415; 514/652; 514/682; 514/714; 514/724; 514/743

(58) Field of Search ................ 514/185, 415, 514/236.2, 652, 682, 714, 724, 743

(56) References Cited

U.S. PATENT DOCUMENTS

| 4,837,399 A | * | 6/1989 | Baker et al. | ................. 514/468 |
| 4,983,637 A | * | 1/1991 | Herman | ...................... 514/724 |
| 5,260,342 A | * | 11/1993 | Herman | ...................... 514/724 |
| 5,270,344 A | * | 12/1993 | Herman | ...................... 514/725 |

* cited by examiner

*Primary Examiner*—Kevin E. Weddington
(74) *Attorney, Agent, or Firm*—Jackson Walker L.L.P.

(57) ABSTRACT

Pharmaceutical formulation, its method of preparation, and its use. The pharmaceutical formulation contains peroxidic species or reaction products resulting from oxidation of an alkene, such as geraniol, by an oxygen-containing oxidizing agent, such as ozone; a penetrating solvent, such as dimethyl sulfoxide; a dye containing a chelated metal, such as hematoporphyrin; and an aromatic redox compound, such as benzoquinone. The pharmaceutical formulation is used to treat horses infected with Sarcocystis protozoal infections.

47 Claims, No Drawings

TARGETED OXIDATIVE THERAPEUTIC FORMULATION

BACKGROUND AND SUMMARY

The present invention relates to a composition containing peroxidic species or oxidation products, its method of preparation, and its use. More specifically, the invention relates to a pharmaceutical composition or formulation which contains: peroxidic species or reaction products resulting from oxidation of an olefinic compound, in a liquid form or in a solution, by an oxygen-containing oxidizing agent; a penetrating solvent; a dye containing a chelated metal; and an aromatic redox compound. The invention also relates to the preparation of the pharmaceutical formulation and its use.

Ozone is a triatomic gas molecule and an allotropic form of oxygen. It may be obtained by means of an electrical discharge or intense ultraviolet light through pure oxygen. After the discovery of ozone by Christian Friedrich Schonbein in 1840, six decades passed without any interest in its medical utilization. At the beginning of World War I, Albert Wolf used the gas for the first time therapeutically when it was administered for the topical healing of infected wounds. However, development of medical applications was impeded by the discovery of antibiotic drugs (sulphonamides and penicillins) in the 1920s along with skepticism associated with the internal applications of ozone gas in the field of medicine. For sixty years, ozone clinical research had been limited to European private practice with anecdotal material not published in peer-reviewed journals. Moreover, the popular misconception that ozone is a serious pollutant, the "free radical" theory of disease, and the antioxidant supplement market have comprehensibly prejudiced medical orthodoxy against its use.

Ozone therapy is a misnomer. Ozone is an extremely reactive and unstable gas with mechanisms of action directly related to the by-products that it generates through selective interaction with organic compounds present in the plasma and in the cellular membranes. The selective reaction of ozone with unsaturated olefins occurs at the carbon—carbon double bond, generating ozonides. Ozone is toxic by itself, and its reaction products, ozonides, are unstable and are not therapeutic by themselves.

Hydrogen peroxide ($H_2O_2$), discovered in 1818, is present in nature in trace amounts. Hydrogen peroxide is unstable and decomposes violently (foams) when in direct contact with organic membranes and particulate matter. Light, agitation, heating, and iron all accelerate the rate of hydrogen peroxide decomposition in solution. Hydrogen peroxide by direct contact ex vivo kills microbes that have low levels of peroxide-destroying enzymes, catalases. For instance, there is no bactericidal effect when hydrogen peroxide is infused into the blood of rabbits infected with peroxide-sensitive E. coli. Moreover, increasing the concentration of peroxide ex-vivo in rabbit or human blood containing E. coli produces no evidence of direct bactericidal activity. The lack of effect of high concentrations of hydrogen peroxide was directly related to the presence of the peroxide-destroying enzyme, catalase. To have any effect, high concentrations of hydrogen peroxide would have to be in contact with the bacteria for significant periods of time. Large amounts of hydrogen peroxide-destroying enzymes, such as catalase, normally present in the blood make it impossible for peroxide to exist in blood for more than a few seconds. One must conclude that hydrogen peroxide introduced into the blood stream by injection or infusion does not directly act as an extracellular germicide in blood or extracellular fluids.

However, hydrogen peroxide does participate in the bactericidal processes within activated macrophage cells. The critical therapeutic criteria for intracellular peroxidation are the selective delivery, absorption and activation of peroxidic carrier molecules into only diseased macrophages, which are believed to be incapable of upgraded catalase and glutathione reductase activity. Infused hydrogen peroxide is a generalized poison whereas targeted intracellular peroxidation is a selective therapeutic tool.

U.S. Pat. No. 4,451,480 to De Villez teaches a composition and method for treating acne. The method includes topically treating the affected area with an ozonized material derived from ozonizing various fixed oil and unsaturated esters, alcohols, ethers and fatty acids.

U.S. Pat. No. 4,591,602 to De Villez shows an ozonide of Jojoba used to control microbial infections.

U.S. Pat. No. 4,983,637 to Herman discloses a method to parenterally treat local and systemic viral infections by administering ozonides of terpenes in a pharmaceutically acceptable carrier.

U.S. Pat. No. 5,086,076 to Herman shows an antiviral composition containing a carrier and an ozonide of a terpene. The composition is suitable for systemic administration or local application.

U.S. Pat. No. 5,126,376 to Herman describes a method to topically treat a viral infection in a mammal using an ozonide of a terpene in a carrier.

U.S. Pat. No. 5,190,977 to Herman teaches an antiviral composition containing a non-aqueous carrier and an ozonide of a terpene suitable for systemic injection.

U.S. Pat. No. 5,190,979 to Herman describes a method to parenterally treat a medical condition in a mammal using an ozonide of a terpene in a carrier.

U.S. Pat. No. 5,260,342 to Herman teaches a method to parenterally treat viral infections in a mammal using an ozonide of a terpene in a carrier.

U.S. Pat. No. 5,270,344 to Herman shows a method to treat a systemic disorder in a mammal by applying to the intestine of the mammal a trioxolane or a diperoxide derivative of an unsaturated hydrocarbon which derivative is prepared by ozonizing the unsaturated hydrocarbon dissolved in a non-polar solvent.

U.S. Pat. No. 5,364,879 to Herman describes a composition for the treatment of a medical condition in a mammal, the composition contains a diperoxide or trioxolane derivative of a non-terpene unsaturated hydrocarbon which derivative is prepared by ozonizing below 35° C. the unsaturated hydrocarbon in a carrier.

Despite the reports on the use of terpene ozonides for different medical indications, terpene ozonides display multiple deficiencies. For example, ozonides of monoterpene, such as myrcene and limonene, flamed out in the laboratory. Consequently, they would be too dangerous to formulate or store.

Furthermore, ozonides of geraniol, a linear monoterpene alcohol, in water or in DMSO did not show any clinical efficacy in three case of viral Varicella Zoster (shingles) and two cases of Herpes Simplex dermatitis.

Thus, there is a need for a safe and effective pharmaceutical formulation or composition utilizing reaction products from the oxidation of an alkene compound.

DETAILED DESCRIPTION

The present invention relates to compositions comprising peroxidic species or reaction products resulting from oxidation of an unsaturated organic compound, in a liquid form or in a solution, by an oxygen-containing oxidizing agent; a penetrating solvent; a chelated dye; and an aromatic redox compound. In one embodiment of the present invention, the essential components include the peroxidic products formed by ozonolysis of an unsaturated alcohol, a stabilizing solvent, metalloporphyrin, and quinone.

The unsaturated organic compound, or the unsaturated olefinic hydrocarbon, for the present invention can be an alkene without a hydroxyl group, or a hydroxyl-containing alkene. Thus, the alkene without a hydroxyl group may be an open-chain unsaturated hydrocarbon, a monocyclic unsaturated hydrocarbon, or a bicyclic unsaturated hydrocarbon. The hydroxyl-containing alkene can be an open-chain unsaturated alcohol, a monocyclic unsaturated alcohol, or a bicyclic unsaturated alcohol.

The unsaturated organic compound may be linear, branched, cyclic, spiral, or complexed with other molecules in its configuration. The unsaturated organic compound may naturally exist in a gaseous liquid or solid state prior to binding with the "activated oxygen."

An open-chain unsaturated hydrocarbons can be: $C_nH_{2n}$, one double bond, n=2–20; $C_nH_{2n-2}$, two double bonds, n=4–20; $C_nH_{2n-4}$, three double bonds, n=6–20; $C_nH_{2n-6}$, four double bonds, n=8–20; $C_{25}H_{40}$, sesterterpene hydrocarbon; or $C_{30}H_{48}$, triterpene hydrocarbon.

A monocyclic unsaturated hydrocarbon can be: $C_nH_{2n-2}$, one double bond+one ring, n=3–20; $C_nH_{2n-4}$, two double bonds+one ring, n=5–20; $C_nH_{2n-6}$, three double bonds+one ring, n=7–20; $C_{25}H_{40}$, sesterterpene hydrocarbon; or $C_{30}H_{48}$, triterpene hydrocarbon.

A bicyclic unsaturated hydrocarbon can be: $C_nH_{2n-4}$, one double bond+two rings, n=4–20; $C_nH_{2n-6}$, two double bonds+two rings, n=6–20; $C_{25}H_{40}$, sesterterpene hydrocarbon; or $C_{30}H_{48}$, triterpene hydrocarbons.

An open-chain unsaturated alcohol can be: $C_nH_{2n}O_m$, one double bond, n=3–20, m=1–4; $C_nH_{2n-2}O_m$, two double bonds, n=5–20, m=1–4; $C_nH_{2n-4}O_m$, three double bonds, n=7–20, m=1–4; $C_nH_{2n-6}O_m$, four double bonds, n=9–20, m=1–4; $C_{25}H_{40}O_m$, m=1–4, sesterterpene alcohols; or $C_{30}H_{48}O_m$, m=1–4, triterpene alcohols.

A monocyclic unsaturated alcohol can be: $C_nH_{2n-2}O_m$, one double bond+one ring, n=3–20, m=1–4; $C_nH_{2n-4}O_m$, two double bonds+one ring, n—5–20, m=1–4; $C_nH_{2n-6}O_m$, three double bonds+one ring, n=7–20, m=1–4; $C_{25}H_{40}O_m$, m=1–4, sesterterpene alcohols; or $C_{30}H_{48}O_m$, m=1–4, triterpene alcohols.

A bicyclic unsaturate alcohol can be: $C_nH_{2n-4}O_m$, one double bond+two rings, n=5–20, m=1–4; $C_nH_{2n-6}O_m$, two double bonds+two rings, n=7–20, m=1–4; $C_{25}H_{40}O_m$, m=1–4, sesterterpene alcohols; or $C_{30}H_{48}O_m$, m=1–4, triterpene alcohols.

Usable unsaturated olefinic hydrocarbons may be unsubstituted, substituted, cyclic or complexed alkenes, hydrazines, isoprenoids, steroids, quinolines, carotenoids, tocopherols, prenylated proteins, or unsaturated fats. The preferred unsaturated hydrocarbons for this invention are alkenes and isoprenoids. The more preferred unsaturated hydrocarbons for this invention are linear isoprenoid alcohols with two to four repeating isoprene groups in a linear chain, such as geraniol, geranylgeraniol, nerol, or linalool.

Isoprenoids are found primarily in plants as constituents of essential oils. While many isoprenoids are hydrocarbons, oxygen-containing isoprenoids also occur such as alcohols, aldehydes, and ketones. In a formal sense, the building block of isprenoid hydrocarbons may be envisaged as the hydrocarbon isoprene, $CH_2$=$C(CH_3)$—CH=$CH_2$, although it is known that isoprene itself is an end-product of isoprenoid biosynthesis and not an intermediate. Isoprenoid hydrocarbons are categorized by the number of isoprene ($C_5H_8$) units they contain. Thus, monoterpenes have 2, sesquiterpenes have 3, diterpenes have 4, sesterterpenes have 5, triterpenes have 6, and tetraterpenes have 8 isoprene units, respectively. Tetraterpenes are much more commonly known as carotenoids.

Limonene and pinene are examples of a monoterpene. Farnesol and nerolidol are examples of a sesquiterpene alcohol. Vitamin $A_1$ and phytol are examples of a diterpene alcohol while squalene is an example of a triterpene. Provitamin $A_1$, known as carotene, is an example of a tetraterpene. Geraniol, a monoterpene alcohol, is liquid in both its oxygen bound and normal states and is safe to living cells.

Based on the total weight of the pharmaceutical formulation, the alkene can vary from about 0.001% to about 30%, preferably from about 0.1% to about 5.0%, and more preferably from about 0.5% to about 3.0%.

The oxygen-containing oxidizing agents for reaction to the unsaturated hydrocarbon may be singlet oxygen, oxygen in its triplet state, superoxide anion, ozone, periodate, hydroxyl radical, hydrogen peroxide, alkyl peroxide, carbamyl peroxide, benzoyl peroxide, or oxygen bound to a transition element, such as molybdenum (e.g. $MoO_5$).

The preferred oxygen-containing oxidizing agents for this invention include ozone, singlet oxygen, and superoxide anion. Ozone is the most preferred oxygen-containing oxidizing agent for binding to the unsaturated hydrocarbon. It is prepared from pure oxygen.

We found that the best method to bind "activated oxygen" to intact geraniol is by ozonation at temperatures between 0–20° C. in the dark in the absence of water or polar solvent. The geraniol "ozonides" were then dissolved and stabilized in 100% dimethylsulfoxide (DMSO) in the dark to prevent premature breakdown of the products. Although not wanting to be bound by any theory, it is believed that the catalytic breakdown of the tetraoxane peroxidic dimer byproduct of geraniol ozonation, which is not an ozonide, occurs inside of cells in the presence of superoxide anion. The final reactive therapeutic agents released are hydrogen peroxide and acetic acid.

Although not wanting to be bound by theory, it is believed that, in general, the reaction between an alkene and ozone in this application proceeds by the Criegee mechanism. According to this mechanism, the initial step of the reaction is a 1,3-dipolar cycloaddition of ozone to the alkene to give a primary ozonide (a 1,2,3-trioxalane). The primary ozonide is unstable and undergoes a 1,3-cycloreversion with the carbonyl compound to give the "normal" ozonide, a 1,2,4-trioxalane.

SCHEME 1

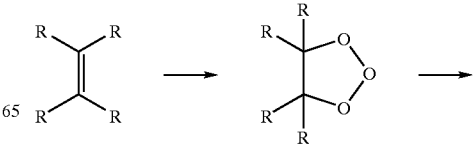

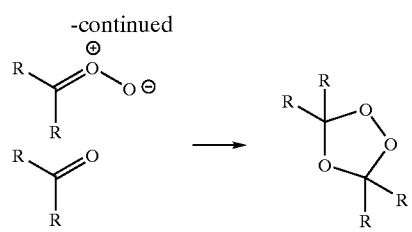

In a side reaction, the carbonyl oxide can enter into a dimerization to give a peroxidic dimer, the 1,2,4,5-tetraoxane.

SCHEME 2

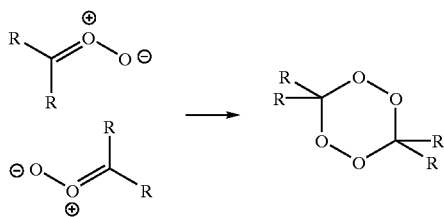

The carbonyl oxide is a strongly electrophilic species, and in the presence of nucleophilic species (e.g. alcohols or water), it undergoes facile nucleophilic addition to give a 1-alkoxyhydroperoxide. Under certain conditions, the 1-alkoxyhydroperoxide can undergo further reaction to give carboxylic acid derivatives.

SCHEME 3

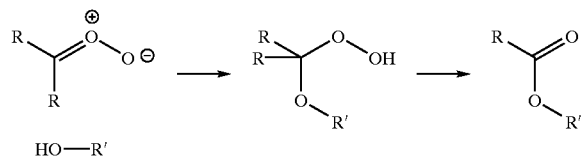

Again, not wanting to be bound by theory, it is believed that during the ozonolysis of the alcohol-containing alkene in the present invention, it is reasonable to expect that three major types of peroxidic products will be present: the normal ozonide, the carbonyl tetraoxane dimer, and the 1-alkoxyhydroperoxide. In the presence of water, some of these peroxidic products may also lead to the presence of organic peracids in the crude product mixture.

The present invention involves the use of DMSO to "stabilize" the initial products of the ozonolysis. Similarly, not wanting to be bound by any theory, it is believed that the stabilization is most likely a simple solvation phenomenon. However, dimethyl sulfoxide is known to be a nucleophile in its own right. Its participation is also possible. as a nucleophilic partner in stabilizing reactive species (for example, as dimethylsulfoxonium salts).

The penetrating solvent for the oxygen-bound unsaturated hydrocarbon may be an emollient, a liquid, a membrane, a micelle, a plasma or a vapor.

Usable penetrating solvents are water fats, sterols, lecithins, phosphatides, pH-buffered saline, ethanol, propylene glycol, dimethyl sulfoxide, methylsulfonylmethane, and polyvinylpyrrolidine. The preferred penetrating solvents include dimethylsulfoxide, polyvinylpyrrolidine, and pH-buffered saline. The most preferred penetrating solvent includes dimethylsulfoxide.

Based on the total weight of the pharmaceutical formulation, the penetrating solvent can vary from about 50% to about 99%, preferably from about 90% to about 98%, and more preferably from about 95% to about 98%.

The "stabilized" peroxidic molecule and its penetrating solvent have been made from components currently used in production regulated by the Food and Drug Administration ("FDA"). These ingredients are the subject of Drug Master Files, Drug Monographs, are found in the USP/NF, or are Generally Recognized As Safe ("GRAS"). The superoxide generating dye and perpetuating agent, also biologically compatible, probably conveniently form a molecular complex.

The other components of the pharmaceutical formulation can include metallo-porphyrin and an aromatic quinone. The propensity of metalloporphyrins to sensitize oxygen under photochemical excitation is well documented, as is the propensity of ferroporphyrins and copper porphyrins to bind oxygen-containing systems.

Researchers of photodynamic therapy have known that the superoxide dye and the perpetuator selectively absorb into infected and dysplastic cells. These diseased cells are fortuitously catalase deficient. The electronic activation of the dye and perpetuator simply requires a milli-volt AC pulse. This requisite pulse is conveniently provided by a beating heart. Moreover, normal cells are not harmed.

Usable dyes, include natural or synthetic dyes. Examples include porphyrins, rose bengal, chlorophyllins, hemins, porphins, corrins, texaphrins, methylene blue, hematoxylin, eosin, erythrosin, flavinoids, lactoflavin, anthracene dyes, hypericin, methylcholanthrene, neutral red, and fluorescein.

For this invention, the preferred dyes can be any natural or synthetic porphyrin, hematoporphyrin, chlorophyllin, rose bengal, their respective congeners, or a combination thereof. The most preferred dyes are naturally occurring porphyrins, such as hematoporphyrin, and rose bengal.

Based on the total weight of the pharmaceutical formulation or composition, the dye can vary from about 0.1% to about 30%, preferably from about 0.5% to about 5%, and more preferably from about 0.8% to about 1.5%.

The dye may be responsive to photon; laser; ionizing radiation; phonon; electrical cardiac electroporation; magnetic or plasma pulse; or continuous flow excitation.

The aromatic redox compound includes any substituted or unsubstituted benzoquinone, naphthoquinone, or anthroquinone. The preferred aromatic redox compound includes benzoquinone, methyl-benzoquinone, naphthoquinone, and methyl-naphthoquinone. The most preferred aromatic redox compound includes substituted or unsubstituted benzoquinone and naphthoquinone.

Based on the total weight of the pharmaceutical formulation, the aromatic redox compound can vary from about 0.01% to about 20.0%, preferably from about 0.1% to about 10%, and more preferably from about 0.1% to about 0.5%.

Useful electron donors for this invention include plasma, an electrical current, ascorbate, and germanium sesquioxide. Preferred electron donors include ascorbate and germanium sesquioxide. The most preferred electron donor is ascorbate in any salt form.

Based on the total weight of the pharmaceutical formulation, the electron donor can vary from about 0.01% to about 20%, preferably from about 1% to about 10%, and more preferably from about 1% to about 5%.

In order to obtain a biological effect in vivo, it is necessary to infuse an ozonolysis peroxidic tetraoxane product of a terpene alcohol, rather than an ozonide, in conjunction with a superoxide generating metallo-porphyrin dye and an aromatic quinone. Although not wanted to be bound by any theory, it is postulated that the preferred pharmaceutical formulation is a combination of biochemical agents that induce recycling autocatalytic oxidation in infected or dysplastic macrophages. The recycling autocatalytic oxidation stimulates targeted apoptosis (cell suicide) through unopposed peroxidation.

The pharmaceutical formulation of this invention was utilized to eliminate Sarcocystis protozoal (*Sarcocystis neurona*) infections in horses afflicted with Equine Protozoal Myeloencephalitis ("EPM"), which is a costly, debilitating, and eventually fatal neurological disease. Examples Two and Three detail the retrospective non-randomized study. The trial evaluated three hundred forty-four consecutive horses diagnosed and treated for EPM.

EPM is currently the most common neurological condition afflicting horses in North and South America. EPM is usually caused by infection of the spinal and cranial nerve tracts with the parasite, *Sarcocystis Neurona*. EPM has been reported to produce numerous syndromes of central nervous system dysfunction. *S. Neurona* has the feral opossum (*Didelphis virginiana*) as its primary host. North and South American horses appear to be an aberrant host for EPM, because the merozoites continually divide in the central nervous system, without encysting. Horses with EPM most commonly have abnormalities of gait, but they also may present with other signs of brain disease, including optic nerve blindness. The disease ranges in severity from mild lameness to sudden recumbence, and clinical signs are progressive.

Serological surveys suggest that approximately 80% of horses in the United States have been exposed to the parasite. Factors found to be significantly associated with the risk of the disease were breed and age of the horse. Quarterhorses and older horses are at a higher risk for infection in comparison to other breeds and ages of horses. Misdiagnosis of equine neurological diseases is common in the wake of the EPM epidemic. Parameters for the accuracy of clinical diagnosis of neurological diseases in the horse were determined from 210 horses in which a definitive pathologic diagnosis was confirmed. The overall efficiency of clinical diagnosis for all diseases was 0.95 although the validity varied from 0.79 to 1.00, the sensitivity varied from 0.73 to 0.95, and the specificity varied from 0.88 to 1.00 for individual disease categories. EPM was over-diagnosed, whereas Eastern Equine Encephalomyelitis, Equine Degenerative Myeloencephalopathy, and traumatic neurological disease were underdiagnosed. Improving the accuracy of diagnosis parameters in clinical practice will allow new diagnostic techniques to be objectively evaluated, resulting in greater efficiency of diagnosis and therapy. EPM is considered a treatable disease, although the response to suppressive antimicrobial treatment is incomplete.

An extensive neurological examination was performed to differentially diagnose EPM from other entities causing loss of limb proprioception. This examination has been proven to be 97% accurate by verification of presence or absence of antibodies in cerebrospinal fluid (CSF).

Currently available treatments for EPM are derived from anti-malarial therapy and are generally based on combination therapies using pyrimethamine and sulfonamides. Clinical experience suggests that these treatments must be continued for at least three to twelve months, and a majority of horses relapse after currently available treatment ceases. There is, therefore, a pressing need for new and curative treatments for this disease.

EXAMPLE 1

Ozonolysis of an alkene may be carried out either in a solvent or neat. In either case, the cooling of the reaction mixture is critical in avoiding explosive decomposition of the peroxidic products of the reaction.

The following general procedure is typical for the ozonolysis of a liquid alkene.

A 1-liter flask fitted with a magnetic stirrer is charged with the alkene (2 moles), and the apparatus is weighed. The flask is surrounded by a cooling bath (ice-water or ice-salt). Once the contents are cooled below 5° C., stirring is begun and a stream of ozone in dry oxygen (typically 3% ozone) is passed through the mixture. It is advantageous to disperse the ozonated oxygen through a glass frit, but this is not necessary for a stirred solution. Periodically, the gas stream is stopped, and the reaction flask is weighed or the reaction mixture is sampled. The gas stream is then re-started.

Once the mass of the reaction flask shows sufficient weight gain, or once the proton magnetic resonance ("$H^1$ NMR") spectrum of the reaction mixture shows the desired reduction in the intensity of the olefinic proton resonances (usually about 50%), the gas flow is stopped.

The ozonolysis may be carried out as above, substituting a solution of the alkene in a solvent non-reactive towards ozone such as saturated hydrocarbons or chlorinated hydrocarbons.

The ozonolysis may be carried out as above, with or without solvent, substituting an alkenol for the alkene without affecting the reaction in any substantive manner.

The reaction mixture is then poured slowly into the cooled penetrating solvent.

EXAMPLE 2

A preferred pharmaceutical formulation of the present invention was prepared as follows:

(1) Sparging an ozone/pure oxygen gas mixture of 120 mg/L up through an alkadiene alcohol, 3,7-dimethyl-2,6-octadien-1-ol (geraniol), at 1 Liter of gas per hour;

(2) Maintaining the temperature of the reaction around 5 degrees C.;

(3) Removing small aliquots of reaction product hourly and measuring by $H^1$ NMR the formation of the peroxidic species or reaction products;

(4) Stopping the reaction when more than about 50% of the available unsaturated bonds have been reacted;

(5) Diluting the product mixture dimethylsulfoxide (1:10) to give a solution or dispersion;

(6) Prior to use in the target biological system, a mixture of hematoporphyrin, rose bengal, and methylnaphthoquinone dry powders was added to the solution or dispersion in sufficient quantity to create a concentration of 20 micromolar of each component dispersed therein when delivered to the target biological system by saline intravenous infusion. Optionally, ascorbate could be added to the formulation prior to use.

EXAMPLE 3

Two preferred formulations are as follows:

A.

| WEIGHT % | INGREDIENT |
|---|---|
| 0.54* | Tetraoxane dimer of acetal peroxide from ozonization of geraniol. |
| 98.00 | DMSO |
| 0.83 | Hematoporphyrin |
| 0.24 | Methylnaphthoquinone |
| 0.39 | Rose Bengal |

*Determined by mass spectroscopy.

B.

| WEIGHT % | INGREDIENT |
|---|---|
| 0.54* | Tetraoxane dimer of acetal peroxide from ozonization of geraniol. |
| 98.00 | DMSO |
| 0.83 | Hematoporphyrin |
| 0.24 | Methylnaphthoquinone |
| 0.39 | Chlorophyllin Sodium-Copper Salt |

*Determined by mass spectroscopy.

EXAMPLE 4

Thirty-three (33) horses were treated via a single injection into the cerebrospinal fluid (CSF) of 0.5 ml of the undiluted preferred pharmaceutical formulation or composition described in Example 3A. Samples of CSF were taken prior to injection to confirm diagnosis. All horses were considered positive by neurological examination for EPM. Laboratory results using Western Blot [analysis] of the CSF were twenty-eight positive (85%), three were non-specific (9%) and two were negative (6%) for antibodies.

Two of the first six horses treated in this group died due to faulty spinal injection technique (head allowed to drop) and were removed from the study. After changing technique, 27 horses were treated without any adverse reactions. Of the remaining 31 horses, twenty-six (85%) became asymptomatic, could be ridden, and returned to normal activity for more than 1 year without relapsing. Three terminal recumbent horses (9%) were euthanized due to continuation of neurological status with little or no improvement. Two horses (6%) with long EPM histories exhibited significant improvement and were able to be ridden but still retained some mild neurological deficit.

The recovery of 85% of these horses is quite remarkable considering the entire group presented with advanced disease, failure on other regimens, and serious neurological symptoms. In comparison, utilizing available orthodox treatments would have yielded an expected partial recovery rate of 10–20%, and the horses would not have been available for riding.

EXAMPLE 5

Three hundred eleven (311) horses were treated in this group over a period of more than 12 months. Treatment consisted of a single jugular intravenous injection of 6 ml. of the preferred pharmaceutical formulation (described in Example 3A) diluted into 50 ml. sterile saline and administered daily for three consecutive days. There were no adverse reactions in this group other than a rare horse becoming lethargic for 2–3 days after completion of treatment.

Two hundred ninety-six (95%) of the horses in this group became asymptomatic within 7–14 days after one treatment course and returned to full training or previous use at an equal or greater level within one month. Four horses (1%) of this group relapsed, exhibiting mild symptoms of EPM, but all returned to full use following a second 3-day treatment series.

The neurological status of eleven horses (4%) improved, allowing them to be ridden and worked. According to the rider, they were not performing at the same level as prior to onset of EPM.

Two horses (<1%) presented with advanced neurological symptoms including cranial nerve deficits. Both of these horses were terminal and recumbent two days prior to presentation, and they did not respond to the preferred pharmaceutical composition. Both horses were euthanized for humane reasons.

The present invention exhibits several distinct advantages over conventional treatments. Intravenous infusion of the formulation of this invention was shown to be remarkably effective in treating EPM.

Ease of administration along with the short duration of the treatment course, provides a more practical and economical option for the client as compared to any other therapy. Traditional treatment series with pyrimethamine and sulfonamides or diclazuril may last more than twelve months per course. Another drawback associated with these longer treatment series is a high relapse rate.

In fact, the recovery times reported were remarkable and unprecedented in the present study that ranged from seven days to three weeks. Also, the intravenous delivery series indicates that the pharmaceutical formulation of the present invention crosses the blood-brain barrier in order to address the infection.

The formulation of the present invention caused no serious complications, deaths, or genetic defects in animal offspring or difficulty with pregnancy (8 mares). The large number of cases in this pilot study, combined with the outstanding results, suggest that the pharmaceutical composition of the present invention is far superior to any currently available treatment for EPM.

The invention may be embodied in other specific forms without departing from the spirit or essential characteristics thereof. The present embodiments are therefore to be considered in all respects as illustrative and not restrictive, the scope of the invention being indicated by the appended claims rather than the foregoing description, and all changes which come within the meaning and range of equivalency of the claims are therefore intended to be embraced therein.

EXAMPLE 6

Ozone at a concentration of 120 mcg/ml at ⅛ L/min was sparged up through 100 ml of 100% myrcene liquid at 5° C., and the vapor was allowed to enter the atmosphere. Static electricity from the chemist set off an explosive flame in the vapor.

Ozonated limonene was created by the same method with precautions against spark generation. The ozonide product was stored in a closet at room temperature in a sealed brown bottle overnight. The next morning the chemist and pharmacist saw fine glass powder and a syrupy chemical splashed inside the closet.

EXAMPLE 7

Ozone (120 micrograms/ml) was bubbled up through 1 L of neat geraniol at 5° C. for 48 hours. The reaction products were diluted 1:9 with DMSO to give a product mixture.

The mixture at 3% was administered intravenously to a patient suffering from Herpes (Varicella) Zoster daily for 3 consecutive days. There was no observable effect or improvement on the patient's Herpes (Varicella) Zoster.

What is claimed is:

1. A pharmaceutical formulation comprising:
   peroxidic species or reaction products resulting from oxidation of an alkene by an oxygen-containing oxidizing agent, wherein the alkene has less than about 35 carbons;
   a penetrating solvent;
   a dye containing a chelated divalent or trivalent metal; and
   an aromatic redox compound.

2. The pharmaceutical formulation of claim 1, wherein the alkene comprises an open-chain unsaturated hydrocarbon, a monocyclic unsaturated hydrocarbon, or a bicyclic unsaturated hydrocarbon.

3. The pharmaceutical formulation of claim 1, wherein the alkene comprises an open-chain unsaturated alcohol, a monocyclic unsaturated alcohol, or a bicyclic unsaturated alcohol.

4. The pharmaceutical formulation of claim 1, wherein the alkene is an hydroxyl-contaning alkene.

5. The pharmaceutical formulation of claim 1, wherein the alkene is in a liquid form, in a solution, or in a dispersion.

6. The pharmaceutical formulation of claim 1, wherein the alkene comprises an isoprenoid.

7. The pharmaceutical formulation of claim 6, wherein the isoprenoid comprises α-terpineol, citronellol, nerol, phytol, menthol, geraniol, geranylgeraniol, linalool, or farnesol.

8. The pharmaceutical formulation of claim 6, wherein the isoprenoid comprises myricene, citrillene, citral, pinene, or limonene.

9. The pharmaceutical formulation of claim 1, wherein the alkene comprises fixed oil-, ester-, fatty acid-, or ether-containing olefin.

10. The pharmaceutical formulation of claim 1, wherein the oxygen-containing oxidizing agent comprises singlet oxygen, oxygen in its triplet state, superoxide anion, periodate, hydroxyl radical, peroxide, or oxygen bound to a transition element.

11. The pharmaceutical formulation of claim 1, wherein the oxygen-containing oxidizing agent comprises ozone.

12. The pharmaceutical formulation of claim 1, wherein the penetrating solvent is a liquid, micelle membrane, emollient, plasma, or vapor.

13. The pharmaceutical formulation of claim 1, wherein the penetrating solvent is dimethylsulfoxide.

14. The pharmaceutical formulation of claim 1, wherein the penetrating solvent is polyvinylpyrrolidine or a pH-buffered saline.

15. The pharmaceutical formulation of claim 1, wherein the penetrating solvent is aqueous solution, fats, sterols, lecithins, phosphatides, ethanol, propylene glycol, or methylsulfonylmethane.

16. The pharmaceutical formulation of claim 1, wherein the dye can be activated by an energy.

17. The pharmaceutical formulation of claim 1, wherein the dye comprises porphyrin or rose bengal.

18. The pharmaceutical formulation of claim 1, wherein the dye comprises chlorophyllin, hemin, corrins, texaphrin, methylene blue, hematoxylin, eosin, erythrosin, lactoflavin, anthracene dye, hypericin, methylcholanthrene, neutral red, or fluorescein.

19. The pharmaceutical formulation of claim 16, wherein the energy comprises photon or electroporation pulse.

20. The pharmaceutical formulation of claim 13, wherein the energy comprises laser, ionizing radiation, phonon, electrical pulse, magnetic field, plasma pulse, gravitational pulse, or continuous flow excitation.

21. The pharmaceutical formulation of claim 1, wherein the metal comprises iron.

22. The pharmaceutical formulation of claim 1, wherein the metal comprises copper, manganese, tin, magnesium, or strontium.

23. The pharmaceutical formulation of claim 1, wherein the aromatic redox compound comprises benzoquinone or naphthoquinone.

24. The pharmaceutical formulation of claim 1 further comprising an electron donor.

25. The pharmaceutical formulation of claim 24, wherein the electron donor comprises ascorbic acid or a pharmaceutical salt thereof.

26. The pharmaceutical formulation of claim 24, wherein the electron donor comprises plasma, electrical current or germanium sesquioxide.

27. A pharmaceutical formulation comprising:
    peroxidic species or reaction products resulting from oxidation of a hydroxyl-containing alkene by a mixture of ozone and oxygen, wherein the hydroxyl-containing alkene has less than about 35 carbons;
    a penetrating solvent;
    a dye containing a chelated divalent or trivalent metal; and
    an aromatic redox compound.

28. The pharmaceutical formulation of claim 27, wherein the hydroxyl-containing alkene comprises an open-chain unsaturated alcohol, a monocyclic unsaturated alcohol, or a bicyclic unsaturated alcohol.

29. The pharmaceutical formulation of claim 27, wherein the hydroxyl-containing alkene is in a liquid form, in a solution, or in dispersion.

30. The pharmaceutical formulation of claim 27, wherein the hydroxyl-containing alkene comprises α-terpineol, citronellol, nerol, linalool, phytol, geraniol, perillyl alcohol, menthol, geranylgeraniol, or farnesol.

31. The pharmaceutical formulation of claim 27, wherein the penetrating solvent is a liquid, micelle membrane, emollient, plasma, or vapor.

32. The pharmaceutical formulation of claim 27, wherein the penetrating solvent is dimethylsulfoxide.

33. The pharmaceutical formulation of claim 27, wherein the penetrating solvent is polyvinylpyrrolidine or a pH-buffered saline.

34. The pharmaceutical formulation of claim 27, wherein the penetrating solvent is aqueous solution, fats, sterols, lecithins, phosphatides, ethanol, propylene glycol, or methylsulfonylmethane.

35. The pharmaceutical formulation of claim 27, wherein the dye comprises porphyrin or rose bengal.

36. The pharmaceutical formulation of claim 27, wherein the dye comprises chlorophyllin, hemin, corrins, texaphrin, methylene blue, hematoxylin, eosin, erythrosin, lactoflavin, anthracene dye, hypericin, methylcholanthrene, neutral red, or fluorescein.

37. The pharmaceutical formulation of claim 27, wherein the metal comprises iron.

38. The pharmaceutical formulation of claim 27, wherein the metal comprises copper, manganese, tin, magnesium, or strontium.

39. The pharmaceutical formulation of claim 27, wherein the aromatic redox compound comprises benzoquinone or naphthoquinone.

40. The pharmaceutical formulation of claim 27 further comprising an electron donor.

41. The pharmaceutical formulation of claim 40, wherein the electron donor comprises ascorbic acid or a pharmaceutical salt thereof.

42. The pharmaceutical formulation of claim 40, wherein the electron donor comprises plasma, electrical current or germanium sesquioxide.

43. A pharmaceutical formulation comprising:
  peroxidic species or reaction products resulting from oxidation of a hydroxyl-containing alkene by a mixture of ozone and oxygen, wherein the hydroxyl-containing comprises α-terpineol, citronellol, nerol, linalool, phytol, geraniol, perillyl alcohol, menthol, geranylgeraniol or farnesol;
  a penetrating solvent, wherein the penetrating solvent comprises dimethylsulfoxide, sterol, lecithin, propylene glycol, or methylsulfonylmethane;
  a dye containing a chelated divalent or trivalent metal, wherein the dye comprises porphyrin, rose bengal, chlorophyllin, hemin, corrins, texaphrin, methylene blue, hematoxylin, eosin, erythrosin, lactoflavin, anthracene dye, hypericin, methylcholanthrene, neutral red, or fluorescein; and
  an aromatic redox compound, wherein the redox compound comprises benzoquinone or naphthoquinone.

44. The pharmaceutical formulation of claim 43, wherein the metal comprises iron, copper, manganese, tin, or magnesium.

45. The pharmaceutical formulation of claim 43 further comprising an electron donor.

46. The pharmaceutical formulation of claim 45, wherein the electron donor comprises ascorbic acid or a pharmaceutical salt thereof.

47. The pharmaceutical formulation of claim 45, wherein the electron donor comprises plasma, electrical current or germanium sesquioxide.

* * * * *